United States Patent
Suenaga et al.

(10) Patent No.: US 8,142,767 B2
(45) Date of Patent: Mar. 27, 2012

(54) COSMETIC HAIR COMPOSITION

(75) Inventors: Koji Suenaga, Tokyo (JP); Akinori Sato, Tokyo (JP); Yutaka Horie, Tokyo (JP)

(73) Assignee: Momentive Performance Materials Japan LLC, Tokyo (JP)

( * ) Notice: Subject to any disclaimer, the term of this patent is extended or adjusted under 35 U.S.C. 154(b) by 1125 days.

(21) Appl. No.: 10/581,714

(22) PCT Filed: Dec. 3, 2004

(86) PCT No.: PCT/JP2004/018015
§ 371 (c)(1),
(2), (4) Date: Jun. 5, 2006

(87) PCT Pub. No.: WO2005/053626
PCT Pub. Date: Jun. 16, 2005

(65) Prior Publication Data
US 2007/0122369 A1    May 31, 2007

(30) Foreign Application Priority Data
Dec. 5, 2003   (JP) .................. 2003-408113

(51) Int. Cl.
*A61Q 5/02* (2006.01)
(52) U.S. Cl. .................. 424/70.12; 424/70.1
(58) Field of Classification Search .......... None
See application file for complete search history.

(56) References Cited

U.S. PATENT DOCUMENTS

| 5,246,694 A | 9/1993 | Birthwistle |
| 6,149,898 A | 11/2000 | Peffly et al. |
| 6,238,656 B1 | 5/2001 | Morita et al. |
| 2003/0143176 A1 | 7/2003 | Liu et al. |

FOREIGN PATENT DOCUMENTS

| CA | 2716438 A1 | 12/2003 |
| EP | 0 468 721 A1 | 1/1992 |
| JP | 04-234309 A | 8/1992 |
| JP | 2000-26726 A | 1/2000 |
| JP | 2000-053769 A | 2/2000 |
| JP | 2000-095661 A | 4/2000 |
| JP | 2000-281523 A | 10/2000 |
| JP | 2001-010935 A | 1/2001 |

OTHER PUBLICATIONS

Supplementary European Search Report issued for application No. EP 04819920.2 on Nov. 11, 2009.

*Primary Examiner* — Jyothsna Venkat
(74) *Attorney, Agent, or Firm* — Foley & Lardner LLP

(57) ABSTRACT

The hair cosmetic composition contains a solvent-containing silicone emulsion (A) which is prepared by emulsifying a mixture of high-molecular-weight polyorganosiloxane (a) obtained by emulsion polymerization and a volatile solvent (b), a surfactant (B) and water (C). The component solvent-containing silicone emulsion (A) is contained at a ratio of 0.1-10 wt % as a total amount of the high-molecular-weight polyorganosiloxane (a) and the volatile solvent (b). And, the component surfactant (B) is contained at a ratio of 0.05-40 wt %. Hair is provided with outstanding smoothness and softness, and particularly good finger combing when rinsing the hair.

2 Claims, No Drawings

COSMETIC HAIR COMPOSITION

TECHNICAL FIELD

The present invention relates to a hair cosmetic composition, and more particularly to a hair cosmetic composition which contains a solvent-containing silicone emulsion and excels in the smoothness in passing fingers through the hair at the time of rinsing hair.

BACKGROUND ART

Conventionally, there have been proposed various types of hair cosmetics which contain a silicone oil (polyorganosiloxane) to provide hair with smoothness, softness, moisture touch and the like.

However, it is general that the silicone oil can provide hair in a dried state with good touch but has a disadvantage that wet hair produces squeaky feel. Therefore, when the silicone oil is contained in a shampoo for washing hair, the fingers did not satisfactorily pass through the hair smoothly. Recently, consumers' demands for the shampoo are miscellaneous such as smooth passing of the fingers through the hair, good touch after drying and the like in addition to the basic performance such as detergency, foaming property and the like.

There is developed a silicone emulsion which is obtained by emulsifying a mixture of a volatile solvent and low-molecular-weight silicone and polymerizing it (e.g., see Patent Document 1) and proposed cosmetics which contain this silicone emulsion (e.g., see Patent Document 2).

There are also proposed a shampoo composition containing an anionic or other type of surfactant, an emulsion of a high-viscosity silicone solution prepared by dissolving in a volatile solvent, and a guar gum cation derivative (e.g., see Patent Document 3).

But, the silicone emulsion and the cosmetics described in the Patent Documents 1 and 2 can give good touch to dry hair but had a disadvantage that fingers do not pass through one's hair smoothly when rinsing.

The shampoo composition described in Patent Document 3 did not provide satisfactory pass of fingers through wet hair.

[Patent Document 1] Japanese Patent Laid-Open Application No. 2000-26726

[Patent Document 2] Japanese Patent Laid-Open Application No. 2000-95661

[Patent Document 3] Japanese Patent Laid-Open Application No. Hei 4-234309

SUMMARY OF THE INVENTION

The present invention has been made in view of the above circumstances and provides a hair cosmetic composition which can provide hair with outstanding smoothness and softness, especially exerts its sufficient effect when hair is wet, and excels in providing remarkable pass of the fingers through the hair when rinsing.

The hair cosmetic composition of the present invention comprises a solvent-containing silicone emulsion (A) which is prepared by emulsifying a mixture of an emulsion (a) of high-molecular-weight polyorganosiloxane (a) obtained by emulsion polymerization and a volatile solvent (b), a surfactant (B) and water (C), wherein the solvent-containing silicone emulsion (A) is contained at a ratio of 0.1 to 10 wt % as a total amount of the high-molecular-weight polyorganosiloxane in the emulsion (a) and the volatile solvent (b), and the surfactant (B) is contained at a ratio of 0.05 to 40 wt %.

In the hair cosmetic composition of the present invention, the surfactant (B) is one or two or more selected from an anionic surfactant, an amphoteric surfactant and a nonionic surfactant, and the composition can be used for hair wash (shampoo).

And, the solvent-containing silicone emulsion (A) can be made to have an average particle diameter of 100 to 500 nm. And, the content ratio of the volatile solvent (b) in the component solvent-containing silicone emulsion (A) can be made 1 to 90 wt % with respect to the total amount of the high-molecular-weight polyorganosiloxane in the emulsion (a) and the volatile solvent (b).

Besides, the viscosity (25° C.) of the high-molecular-weight polyorganosiloxane in the emulsion (a) can be made 10,000 to 30,000,000 mPa·s.

According to the hair cosmetic composition of the present invention, remarkable smoothness and softness which cannot be obtained by a conventional one can be given to both wet hair and dry hair and especially exerts remarkable finger-combing at the time of hair rinsing.

BEST MODE FOR IMPLEMENTING THE INVENTION

Preferable embodiments of the present invention will be described. It is to be understood that the present invention is not limited to the following embodiments.

The hair cosmetic composition of the embodiments of the present invention contains a solvent-containing silicone emulsion (A), a surfactant (B) and water (C). And, the solvent-containing silicone emulsion (A) is obtained by mixing an emulsion of high-molecular-weight polyorganosiloxane obtained by emulsion polymerization and a volatile solvent (b) and by emulsifying them mechanically.

In the embodiments, the component high-molecular-weight polyorganosiloxane emulsion (a) can be produced by conducting emulsion polymerization of silanol group-end polydiorganosiloxane (a1) in an emulsion which contains the silanol group-end polydiorganosiloxane (a1), an ionic surfactant (a2), a polymerizing catalyst (a3) and water (a4).

The component (a1) which is used as a monomer which gives high-molecular-weight polyorganosiloxane by the emulsion polymerization is polydiorganosiloxane which has a molecular chain end blocked with a silanol group and is represented by a general formula $HO(R_2SiO)_nH$.

In the formula, R represents mutually same or different substituted or unsubstituted monovalent hydrocarbon groups and n represents a value which is made to have a viscosity of 10 to 3,000 mPa·s at 25° C. This polydiorganosiloxane may be called as $\alpha,\omega$-dihydroxypolydiorganosiloxane hereinafter. Its molecular structure is linear as represented by the above general formula but may partly include a branch structure if the molecular chain end is blocked with the silanol group.

And, polydiorganosiloxane which is represented by a general formula $R_3SiO(R_2SiO)_nSiR_3$ (where, R represents mutually same or different substituted or unsubstituted monovalent hydrocarbon groups and n represents a value which is made to have a viscosity of 3,000 mPa·s or below at 25° C.) and has the terminal blocked with a triorganosilyl group can be used as a terminal blocking agent together with $\alpha,\omega$-dihydroxypolydiorganosiloxane for the emulsion polymerization. In this case, the terminal of the high-molecular-weight polyorganosiloxane produced by the emulsion polymerization is blocked with the triorganosilyl group. The usage of the terminal blocking agent can be determined depending on a viscosity of a desired high-molecular-weight polyorganosiloxane.

In the general formula $HO(R_2SiO)_nH$ or the general formula $R_3SiO(R_2SiO)_nSiR_3$, R which is bonded to the silicon atom is a substituted or unsubstituted monovalent hydrocarbon group. Examples of the unsubstituted monovalent hydrocarbon group are a linear or branched alkyl group such as a methyl group, an ethyl group, a propyl group, a hexyl group, an octyl group, a decyl group, a hexadecyl group or an octadecyl group; an aryl group such as a phenyl group, a naphthyl group or a xenyl group; an aralkyl group such as a benzyl radical, a β-phenylethyl group, a methylbenzyl group, a naphthylmethyl group or a 2,4-diphenyl-4-methyl pentyl group; and a cycloalkyl group such as a cyclohexyl group or a cyclopentyl group.

Examples of the substituted monovalent hydrocarbon group include a group which has the hydrogen atom of the above-described unsubstituted monovalent hydrocarbon group substituted by a halogen atom such as fluorine or chlorine, for example, a 3,3,3-trifluoropropyl group or a 3-fluoropropyl group.

Since, the high-molecular-weight polyorganosiloxane obtained by the emulsion polymerization has a low surface tension, a good spreading property when coated, remarkable expansion, repellency and luster and no bioactivity, 85 mol % or more of R in the molecule is desirably a methyl group, and it is particularly desirable that substantially all of R is the methyl group. Therefore, what is desirable as the component (a1) is α,ω-dihydroxypoly(dimethylsiloxane) and a copolymerized polysiloxane which has a part of its dimethylsiloxane unit substituted by a methylethyl siloxane unit, a methyl hexyl siloxane unit, a methylphenyl siloxane unit or a diphenyl siloxane unit. Among them, the α,ω-dihydroxypoly(dimethylsiloxane) is particularly desirable.

The component (a2) ionic surfactant is a component necessary to emulsify the above-described silanol group-end polydiorganosiloxane (a1) in water, and an anionic surfactant, a cationic surfactant and an amphoteric surfactant can be used.

As the anionic surfactant, alkylbenzenesulfonate, unsaturated aliphatic sulfonic acid, hydroxide aliphatic sulfonic acid, alkyl sulfuric acid, alkyl ether sulfate, alkyl phosphoric acid, alkylether phosphoric acid, alkylether carboxylic acid and salts of them can be used. The alkyl group of these anionic surfactants is desirably long chained and suitably has, for example, a carbon number of 6 to 20, and more preferably a carbon number of 8 to 18. And, the alkyl ether sulfate, the alkylether phosphoric acid and the alkylether carboxylic acid have 1 to 20 ethylene oxide groups or propylene oxide groups per molecule and preferably 1 to 10 ethylene oxide groups.

Specific examples of the anionic surfactant are as follows. Specifically, examples of the alkylbenzenesulfonate are hexyl benzenesulfonic acid, octyl benzenesulfonic acid, decyl benzenesulfonic acid, dodecyl benzenesulfonic acid, tetradecyl benzenesulfonic acid, hexadecyl benzenesulfonic acid, octadecyl benzenesulfonic acid and salts of them. Examples of the unsaturated and(or) hydroxidealiphatic sulfonic acid are dodecene sulfonic acid, tetradecene sulfonic acid, hexadecene sulfonic acid, hydroxydodecane sulfonic acid, hydroxytetradodecane sulfonic acid, hydroxyhexadecane sulfonic acid and salts of them. Examples of the alkyl sulfuric acid are octylsulfuric acid, dodecylsulfuric acid, tetradecylsulfuric acid, hexadecylsulfuric acid, octadecylsulfuric acid and salts of them. Examples of the alkyl ether sulfate are polyoxyethylene (2) lauryl ether sulfate, polyoxyethylene (3) lauryl ether sulfate, polyoxyethylene (4) lauryl ether sulfate, polyoxyethylene (3) cetyl ethereal sulfate, polyoxyethylene (6) stearyl ethereal sulfate, polyoxyethylene (4) nonyl phenyl ethereal sulfate and salts of them. Examples of the alkyl phosphoric acid are lauryl phosphoric acid, cetyl phosphoric acid and salts of them. Examples of the alkylether phosphoric acid are dipolyoxyethylene (10) lauryl ether phosphoric acid, tripolyoxyethylene (4) lauryl ether phosphoric acid, tripolyoxyethylene (5) cetyl ether phosphoric acid and salts of them. And examples of the alkylether carboxylic acid are polyoxyethylene (4) lauryl ether carboxylic acid, polyoxyethylene (10) lauryl ether carboxylic acid and salts of them.

The anionic surfactant which takes a form of an acid is useful as the polymerizing catalyst (corresponding to the component (a3) described later) for α,ω-dihydroxypoly(dimethylsiloxane) but, if its catalytic action is not used, it may be used in a form of a water-soluble salt or a neutralized salt. As to the salt, the contribution of a hydrophilic portion to a lipophilic portion of the molecule becomes large, and an emulsify action is often larger than that of the acid itself. As a type of salt, sodium salt, potassium salt, ammonium salt and amine salt such as triethanol amine are desirable in view of the emulsifying effect.

Another group of the component (a2) ionic surfactant is a cationic surfactant. As the cationic surfactant, quaternary ammonium salt or hydroxy quaternary ammonium salt, and particularly one having at least one of aliphatic groups, which quaternize the amino group, long chained, for example, one having a carbon number of 6 to 20 and more preferably a carbon number of 8 to 18 is appropriate.

Examples of the cationic surfactants are lauryl trimethyl ammonium hydroxide, stearyl trimethyl ammonium hydroxide, dioctyl dimethyl ammonium hydroxide, distearyl dimethyl ammonium hydroxide, lauryl trimethyl ammonium chloride, stearyl trimethyl ammonium chloride, cetyltrimethyl ammonium chloride, dicocoyl dimethyl ammonium chloride, distearyl dimethyl ammonium chloride, benzalkonium chloride and stearyl dimethylbenzyl ammonium chloride, and they can be used alone or as a mixture of two or more of them.

The cationic surfactant has a low catalytic action, and it is desirable to use it together with a polymerizing catalyst, for example, an alkali metal hydroxide such as lithium hydroxide, sodium hydroxide, potassium hydroxide or rubidium hydroxide.

The component (a2) ionic surfactant may be an amphoteric surfactant. Examples of the amphoteric surfactant are carbobetaine-based, amide betaine-based, sulfo betaine-based, hydroxy sulfo betaine-based, imidazolinium betaine-based and amine oxide-based ones having an alkyl group, an alkenyl group or an acyl group with a carbon number of 8 to 24. Specifically, they are lauryl dimethylaminoacetic acid betaine, stearyl dimethylaminoacetic acid betaine, lauric acid amidopropyl betaine, coconut oil fatty acid amidopropyl betaine, lauryl hydroxy sulfo betaine, 2-alkyl-N-carboxymethyl-N-hydroxyethyl imidazolinium betaine and lauryldimethyl amine oxide.

The above-described various types of ionic surfactants can be used within various groups and/or between the individual groups. It is not desirable to use an anionic surfactant and a cationic surfactant which have a different ionic property together.

A nonionic surfactant can also be used together with the ionic surfactant. Examples of the nonionic surfactant are glycerine fatty acid ester, propylene glycol fatty acid ester, sorbitan fatty acid ester, polyoxyethylene sorbitan fatty acid ester, polyoxyethylene alkylether, polyethylene glycol fatty acid ester, polyoxyethylene hardened caster oil, and alkyl alkanolamide.

More specifically, examples of the nonionic surfactant are as follows. There are glyceryl monostearate, glyceryl monooleate and glyceryl monocaprylate as the glycerine fatty acid ester; propylene glycol monostearate as the propylene glycol fatty acid ester; sorbitan monostearate, sorbitan monooleate and coconut oil fatty acid sorbitan as the sorbitan fatty acid ester; polyoxyethylene sorbitan monolaurate (6E.O.), coconut oil fatty acid polyoxyethylene sorbitan (20E.O.), polyoxyethylene sorbitan monostearate (6E.O.) and polyoxyethylene sorbitan monostearate (20E.O.) as the polyoxyethylene sorbitan fatty acid ester; polyoxyethylene (4) lauryl ether, polyoxyethylene (5) lauryl ether, polyoxyethylene (23) lauryl ether, polyoxyethylene (7) cetyl ether and polyoxyethylene (13) cetyl ether as the polyoxyethylene alkyl ether; polyethylene glycol monolaurate (12E.O.) and polyethylene glycol monostearate (14E.O.) as the polyethylene glycol fatty acid ester; polyoxyethylene hardened ricinus oil (25E.O.) and polyoxyethylene hardened ricinus oil (40E.O.) as the polyoxyethylene hardened caster oil; and diethanol amid laurate and coconut oil fatty acid diethanol amid as the alkyl alkanol amide.

The blending amount of the component (a2) ionic surfactant can be determined as desired depending on a purpose, considering an occasion of using it as a polymerizing catalyst. A typical example of the blending amount is desirably 0.5 to 100 parts by weight of the ionic surfactant (a2) to 100 parts by weight of the component (a1) silanol group-end polydiorganosiloxane, more desirably 1 to 50 parts by weight, and most desirably 2 to 10 parts by weight. If it is less than 0.5 part by weight, the emulsion of the high-molecular-weight polyorganosiloxane (a) obtained by the emulsion polymerization is poor in stability, and separation might occur. If it exceeds 100 parts by weight, the emulsion might have a thickened viscosity, resulting in poor fluidity. Where two or more types of ionic surfactants are used together and a nonionic surfactant is also used at the same time, the used amount is considered as a total amount.

The component (a3) is a catalyst used for the emulsion polymerization of the component (a1) silanol group-end polydiorganosiloxane. The polymerization of the silanol group-end polydiorganosiloxane (a1) is a polymerization involving dehydration of a terminal hydroxyl group, namely polycondensation, and an anionic catalyst or a cationic catalyst can be used.

Examples of the anionic catalyst are mineral acid or inorganic acid and organic acid. Examples of the mineral acid or inorganic acid are hydrochloric acid, sulfuric acid, phosphoric acid and sulfamic acid, and examples of the organic acid are carboxylic acid (including formic acid), sulfonic acid, sulfamic acid and monoester sulfate. In the organic acids, sulfonic acid and monoester sulfate include those with large contribution of an organic group and having surface activity.

Sulfonic acid and monoester sulfate having surface activity can be selected as required from the specific examples (not salt-formed) of the above-described component (a2) anionic surfactant. Specific examples of the anionic surfactant which is also desirable as the anionic catalyst are alkylbenzene sulfonate, unsaturated aliphatic sulfonic acid, hydroxide aliphatic sulfonic acid, alkyl naphthylsulfonic acid, alkyl sulfuric acid and polyoxyethylene alkyl ether sulfate.

Examples of the cationic catalyst include water-soluble inorganic base and organic base compounds. Examples of the inorganic base are alkali metal hydroxide, alkaline-earth metal hydroxide and alkali metal carbonate.

Examples of the water-soluble organic base include a quaternary ammonium hydroxide compound. In the organic bases, a quaternary ammonium compound having high contribution of its organic group has a function as the cationic surfactant. Specific examples are a quaternary ammonium hydroxyl compound and its salts. The quaternary ammonium salt has low catalytic action, so that it is advisably activated when used together with the alkali metal hydroxide. In addition, examples includes a salt of weak acid and strongly-basic salt showing basic in water, for example, an alkali metal salt of an organic acid (including alkali metal salt of carbolic acid/phenol) other than the above-described alkali metal carbonate.

Generally, those having weak action as the base are often weak in catalytic action, so that the quaternary ammonium salt is desirably activated by simultaneously using alkali metal hydroxide in advance or at the time of using as a catalyst as described above. These ionic catalysts can be used in combination within the individual groups and/or between the individual groups.

Thus, some of the ionic polymerization catalysts have a function as the ionic surfactant, so that when the used ionic surfactant has a catalyst activity, its catalyst activity can be used to reduce the amount of another catalyst or to omit its use. It is preferable in view of the relationships between the ionic characteristics of the surfactant and the catalyst that an anionic catalyst is used when an anionic surfactant is used, and a cationic catalyst is used when a cationic surfactant is used.

Generally, the ionic surfactant of which hydrophilic portion has a salt form is good in emulsifying property but often does not show polymerization activity. Therefore, the surfactant in such a salt form can also be made to function as the catalyst by converting into at least partly an acid or base form during the polymerization depending on the situation after forming the emulsion.

The blending amount of the polymerizing catalyst (a3) can be determined arbitrarily if the required polymerization activity can be obtained for the silanol group-end polydiorganosiloxane (a1). For example, 0.001 to 10 parts by weight of polymerizing catalyst (a3) is preferable, and 0.01 to 5 parts by weight is particularly preferable for 100 parts by weight of the silanol group-end polydiorganosiloxane (a1). When the ionic surfactant has a salt form, for example, when it is sulfonate, the catalyst such as mineral acid acts on the surfactant salt to convert it into a free acid, thereby showing catalyst activity. Therefore, where the surfactant having a salt form is used, the blending amount of the polymerization catalyst is desirably determined considering a stoichometric amount for converting the surfactant into a free acid.

Water as the component (a4) is a medium for dispersing and emulsifying the silanol group-end polydiorganosiloxane (a1). The used amount of the water (a4) is normally 40 to 900 parts by weight to 100 parts by weight of the silanol group-end polydiorganosiloxane (a1), and desirably an amount such that the concentration of the silanol group-end polydiorganosiloxane (a1) in the emulsion becomes 10 to 70 wt %.

In the embodiment of the present invention, the component high-molecular-weight polyorganosiloxane emulsion (a) can be produced by polymerizing (emulsion polymerization) the silanol group-end polydiorganosiloxane (a1) in the emulsion containing the above-described silanol group-end polydiorganosiloxane (a1), the ionic surfactant (a2), the polymerizing catalyst (a3) and the water (a4).

First, the component (a1) such as α,ω-dihydroxypolydiorganosiloxane, the ionic surfactant (a2), the polymerizing catalyst (a3) and the water (a4) are mixed. Their mixing order is arbitrary. For example, the ionic surfactant (a2) is mixed to dissolve in the water (a4) in a stirring vessel, then the terminal silanol group-containing polyorganosiloxane (a1) is added to the dissolved solution while stirring to perform preliminary emulsification. Then, it is preferable to emulsify by use of a pressure homogenizer, an ultrasonic homogenizer, a colloid mill, aline mixer, a sonolator, a homomixer, and an emulsion machine having an anchor mixer and a homomixer or an anchor mixer and a disper mixer as one. At the time of preliminary emulsification, these emulsion machines can also be used. And, after the emulsification, water is further added if necessary to perform homogeneous emulsification and dispersion.

When salt is used as the ionic surfactant (a2) to emulsify, an acid or a base (normally, a mineral acid or alkali metal hydroxide) is added prior to the completion of polymerization to convert at least part of the salt of the surfactant into a free acid (e.g., sulfonic acid) or a base (e.g., quaternary ammonium hydroxide), so that at least part of the polymerizing catalyst (a3) can be formed on site.

When the stirring is continued, high-molecular weight polyorganosiloxane is synthesized by polycondensation reaction of the component (a1) terminal silanol group, and an emulsion containing them is formed. To obtain polyorganosiloxane having a higher polymerization degree, it is desirable that the polycondensation reaction temperature is lower. Meanwhile, if cooling is excessive, the stability of the emulsion is deteriorated. Therefore, a preferable condensation condition is in a range of a freezing point of the emulsion to 80° C., more preferably in a range of the emulsion's freezing point to 50° C., and most preferably in a range of the emulsion's freezing point to 25° C., for 2 to 48 hours, but a longer time may be taken if necessary.

When a desired polymerization degree is attained, the polymerization reaction is stopped. To stop the polymerization reaction, the emulsion using an anionic surfactant may be neutralized with another basic substance such as sodium hydroxide, potassium hydroxide, sodium carbonate, potassium carbonate, ammonium carbonate, potassium acetate, triethanolamine, amine, ammonia water or the like. The emulsion using a cationic surfactant is neutralized with an acid substance such as acetic acid, formic acid, phosphoric acid, sulfuric acid, hydrochloric acid or the like.

The nonionic surfactant which is used together with an ionic surfactant can be used before or after the emulsion formation, during the emulsion polymerization, or after the polymerization.

Besides, in order to provide hair with bounce and moist feel, a reactive silane compound can be added to the high-molecular-weight polyorganosiloxane emulsion (a) which is obtained by the emulsion polymerization to convert into polyorganosiloxane having a crosslinked structure or polyorganosiloxane having a functional group such as an amino group. Examples of the reactive silane compound include methyltrimethoxysilane, methyltriethoxysilane, tetramethoxysilane, tetraethoxysilane, phenyltrimethoxysilane, phenyltriethoxysilane, vinyltriethoxysilane, 3-chloropropyltrimethoxysilane, 3-glycidoxypropyltrimethoxysilane, 3-aminopropyltriethoxysilane, N-(2-aminoethyl)-3-aminopropyltrimethoxysilane, and N-(2-aminoethyl)-3-aminopropylmethyldimethoxysilane, and one or two or more of them can be added during or after the emulsion polymerization.

According to the embodiments of the present invention, the mixture of the high-molecular-weight polyorganosiloxane emulsion (a) obtained by the emulsion polymerization and the volatile solvent (b) are mechanically emulsified to obtain the component (A) solvent-containing silicone emulsion. The "volatility" of the volatile solvent shows a property that a substance becomes vapor under specified temperature and pressure conditions, namely a property having a boiling point. And, it may be determined to indicate a property that when 1 g of a substance is left standing at 150° C. for 24 hours, its 90% or more exerts.

The volatile solvent of the component (b) is also a solvent which disperses the high-molecular-weight polyorganosiloxane in the component (a). As the volatile solvent (b), the following can be used. They are aliphatic hydrocarbons such as n-hexane, gasoline, rubber solvent, mineral spirit, kerosene and isoparaffinic hydrocarbon, aromatic hydrocarbons such as benzene, toluene and xylene, fatty acid esters such as isodecyl neopentanoate, ethylhexyl isononanoate and isononyl isononanoate, cyclic or straight-chain siloxanes, silicon compounds and the like.

Here, the cyclic siloxane is represented by a general formula $(R_2SiO)_n$ where R is mutually same or different substituted or unsubstituted monovalent hydrocarbon groups, and n is a value of 3 to 7. R which is bonded to a silicon atom is the same as that of the above-described α,ω-dihydroxypolydiorganosiloxane of the component (a1).

Examples of the cyclic siloxane are hexamethyl cyclotrisiloxane, octamethyl cyclotetrasiloxane, decamethyl cyclopentasiloxane, dodecamethyl cyclohexasiloxane, 1,3,5,7-tetramethyl-1,3,5,7-tetraethyl cyclotetrasiloxane, octaethyl cyclotetrasiloxane, 1,3,5,7-tetramethyl-1,3,5,7-tetraphenyl cyclotetrasiloxane and (3,3,3-trifluoropropyl)methyl cyclotrisiloxane.

The straight-chain siloxane is represented by a general formula $R_3SiO(R_2SiO)_nSiR_3$. In the formula, R represents the mutually same or different substituted or unsubstituted monovalent hydrocarbon groups, and n represents a value which provides a viscosity of 6 mPa·s or less at 25° C.

R to be bonded to the silicon atom is the same as the above-described component (a1) α,ω-dihydroxypolydiorganosiloxane. Examples of the straight-chain siloxane are hexamethyldisiloxane, hexaethyldisiloxane, octamethyltrisiloxane, decamethyltetrasiloxane, dodecamethylpentasiloxane, 3-ethyl-1,1,1,3,5,5,5-heptamethyltrisiloxane, 3-prolyl-1,1,1, 3,5,5,5-heptamethyltrisiloxane, 3-butyl-1,1,1,3,5,5,5-heptamethyltrisiloxane and 1-butyl-1,1,3,3,5,5,7,7,7-nonamethyltetrasiloxane.

The silicon compound to be used as the volatile solvent of the component (b) is a silane compound represented by a general formula $R_nSi(OSiR_3)_{(4-n)}$. In the formula, R denotes mutually same or different substituted or unsubstituted monovalent hydrocarbon groups, and n is an integer of 1, 2, 3. R which is bonded to the silicon atom is the same as the above-described α,ω-dihydroxypolydiorganosiloxane of the component (a1). Specifically, examples of the silane compound are trimethyl(trimethyl siloxy)silane, dimethyldi(trimethyl siloxy)silane, and methyltris(trimethyl siloxy)silane.

R directly connected to silicon of these cyclic or straight-chain siloxane and silicon compound is preferably a methyl group and an ethyl group, and more preferably the methyl group, in view of the effects of smoothness, softness, and remarkable finger-combing when rinsing.

As the volatile solvent, not only those described above but also the compounds represented by the following chemical formulas can also be used. In addition, these volatile solvents may be used alone or as a mixture of at least two of them.

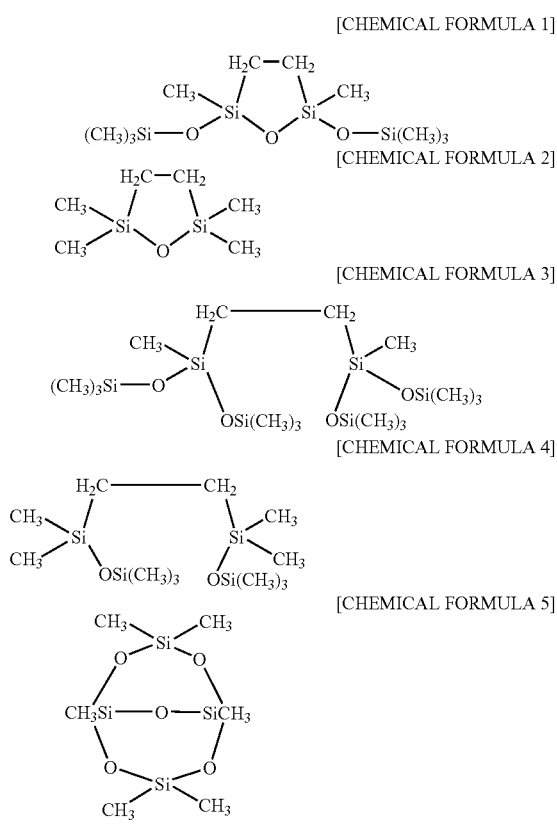

As a mechanical emulsifying method, a known method can be used. The above-described all emulsion machines, namely, a pressure homogenizer, an ultrasonic homogenizer, a colloid mill, a line mixer, a sonolator, a homomixer, and an emulsion machine having an anchor mixer and a homomixer or an anchor mixer and a disper mixer as one can be used.

A surfactant is used at the time of emulsifying. As the surfactant, any of the above-described anionic surfactant, cationic surfactant, nonionic surfactant and amphoteric surfactant may be used, and they can be used alone or as a mixture of two or more. These surfactants can be used in the same amount as that described above. The surfactant can be used in a reduced amount in a range that the effect of the present invention and the stability of the emulsion are not deteriorated or its use can be omitted. In other words, the surfactant which is previously contained in the silicone emulsion obtained by the emulsion polymerization can be used to emulsify.

In the embodiment of the present invention, the viscosity of the high-molecular-weight polyorganosiloxane in the emulsion (a) obtained by the emulsion polymerization is desirably 10,000 to 30,000,000 mPa·s at 25° C. More preferably, it is 100,000 to 10,000,000 mPa·s lithe viscosity of the high-molecular-weight polyorganosiloxane in-the-component (a) is less than 10,000 mPa·s, the effects of smoothness and softness after drying the hair are insufficient, and the high-molecular-weight polyorganosiloxane having a viscosity of exceeding 30,000,000 mPa·s has a long reaction time for the emulsion polymerization reaction, and the production is substantially difficult.

The volatile solvent (b) is desirably contained in a ratio of 1 to 90 wt %, and more desirably a ratio of 5 to 70 wt %, with respect to a total amount of the high-molecular-weight polyorganosiloxane (a) and the volatile solvent (b). If the volatile solvent content is less than 1 wt % or exceeds 90 wt %, the effects of smoothness and softness of the present invention and also excellent finger-combing at the time of rinsing cannot be provided.

It is determined that the obtained solvent-containing silicone emulsion (A) has an average particle diameter of 100 to 500 nm and more preferably 150 to 350 nm. If the average particle diameter is less than 100 nm, the emulsion particles hardly remain on the hair, and the dried hair is not provided with satisfactory effects of smoothness and softness. If the average particle diameter exceeds 500 nm, the emulsion stability might be deteriorated, and excellent finger-combing at the time of rinsing cannot be provided.

The blending amount of the component solvent-containing silicone emulsion (A) is 0.1 to 10 wt %, preferably 0.5 to 8 wt %, and more preferably 1 to 6 wt % of the entire cosmetic composition as a total amount of the high-molecular-weight polyorganosiloxane (a) and the volatile solvent (b). If the blending amount is less than 0.1 wt %, the hair is not provided with the effects of smoothness and good finger-combing, and if it exceeds 10 wt %, it is not desirable because silicone deposits on the hair more than necessary, and tackiness or squeak is felt.

As the surfactant of the component (B), any of the anionic surfactant, the cationic surfactant, the nonionic surfactant and the amphoteric surfactant can be used, and they can be used alone or as a mixture of two or more of them.

As the anionic surfactant, the cationic surfactant and the amphoteric surfactant, all the surfactants exemplified as the ionic surfactant (a2) to be used when the high-molecular-weight polyorganosiloxane (a) is produced by the emulsion polymerization, can be used.

Specifically, examples of the anionic surfactant are alkylbenzenesulfonate, unsaturated aliphatic sulfonic acid, hydroxide aliphatic sulfonic acid, alkyl sulfuric acid, alkyl ether sulfate, alkyl phosphoric acid, alkylether phosphoric acid, alkylether carboxylic acid and their sodium salts, potassium salts, triethanolamine salts and the like.

Examples of the cationic surfactant are lauryl trimethylammonium hydroxide, stearyl trimethylammonium hydroxide, dioctyl dimethylammonium hydroxide, distearyl dimethylammonium hydroxide, lauryl chloride trimethylammonium, stearyl chloride trimethylammonium, cetyltrimethylammonium chloride, dicocoyl dimethylammonium chloride, distearyl dimethylammonium chloride, benzalkonium chloride, stearyl chloride dimethylbenzylammonium and the like.

Examples of the amphoteric surfactant are lauryl dimethyl aminoacetate betaine, stearyl dimethyl aminoacetate betaine, lauric acid amidopropylbetaine, coconut fatty acid amidopropylbetaine, laurylhydroxysulfobetaine, 2-alkyl-N-carboxymethyl-N-hydroxyethylimidazorinium betaine, lauryldimethyl amine oxides and the like.

The type of surfactant is selected depending on compatibility with other components in the hair cosmetic. For example, when a target hair cosmetic composition is an anionic composition such as a shampoo, at least one surfactant selected from an anionic surfactant, an amphoteric surfactant and a nonionic surfactant is used preferably, and when the target hair cosmetic composition isacationic composition suchasarinse, a conditioner or the like, at least one surfactant selected from the cationic surfactant, the amphoteric surfactant and the nonionic surfactant is used preferably. The nonionic surfactant can be blended stably with both the anionic composition and the cationic composition and used preferably.

As the nonionic surfactant, all the above-described surfactants can be used. For example, glycerin fatty acid ester, propylene glycol fatty acid ester, sorbitan fatty acid ester, polyoxyethylene sorbitan fatty acid ester, polyoxyethylene alkylether, polyethylene glycol fatty acid ester, polyoxyethylene hardened caster oil and alkyl alkanolamide can be used. Because the obtained emulsion has good stability, those having an HLB value of 6 to 20 are desirably used together.

The blending amount of the surfactant (B) is preferably in a range of 0.05 to 40 wt % of the whole cosmetic composition. Where the target hair cosmetic composition is a shampoo composition, the blending amount is more preferably in a range of 5 to 30 wt %, and where the target hair cosmetic composition is a rinse or conditioner composition, the blending amount is more preferably in a range of 0.1 to 20 wt %. If it is less than 0.05 wt %, it is hard to disperse the individual components suitably. And, if it exceeds 40 wt %, the cosmetic composition is degraded in stability and sense of use (usability, comfortable use). A blending amount of water as dispersion medium for the emulsion is preferably in a range of 20 to 90 wt % of the whole composition, and more preferably 30 to 80 wt %.

Specific examples of the hair cosmetic composition according to the present invention are shampoos, rinses, conditioners, treatments, hair styling products, hair mousses, hair creams, gels and the like. The individual cosmetics have different purposes but have the same characteristics of providing the hair with a smooth touch. Especially, the hair cosmetic composition of the present invention provides quite outstanding passing of the fingers through the hair at the time of rinsing, and it can provide the wet hair with remarkable smoothness, and it is suitable as hair washing cosmetics such as a shampoo.

In addition to the above-described components, to the hair cosmetic composition according to the embodiment of the present invention can be blended, as cosmetic preparation components in accordance with the purpose, an oil content such as liquid paraffin, squalane, lanolin derivative, higher alcohol or various types of ester oils, a moisturizer such as ethylene glycol, propylene glycol, glycerin or diethylene glycol mono-ethyl ether, a pearl gloss-providing agent such as ethylene glycol monostearate or ethylene glycol distearate, a thickener such as carboxy vinyl polymer, hydroxymethyl cellulose, hydroxyethyl cellulose, sodium chloride or ammonium chloride, a cationized polymer such as cationized cellulose, a silicone derivative such as dimethylsilicone, methylphenyl silicone, polyether-modified silicone, amino-modified silicone, fatty acid-modified silicone, fluorine-modified silicone, cyclic silicone, alkyl-modified silicone or alcohol-modified silicone other than the component (A), an ultraviolet absorber, a fragrance, a preservative, an anti dandruff agent, a coloring agent, a pH adjuster and an oxidation inhibitor.

To blend these cosmetic preparation components, in other way for the preparation of cosmetics by adding the cosmetic preparation components to mix with the solvent-containing silicone emulsion (A), all or part of the cosmetic preparation components other than the component (A) is previously emulsified by an emulsion machine such as a homogenizer, a colloid mill or a line mixer or homogeneously mixed by a stirrer, and the component (A) is added to the mixture to prepare the cosmetics of the present invention or the cosmetics preparation components can be further added to prepare the cosmetic of the present invention.

The hair cosmetic composition of the present invention can provide both wet hair and dry hair with outstanding smoothness and softness, which could not be provided by the conventional hair cosmetic composition, and exerts particularly excellent finger-combing when rinsing the hair.

EXAMPLES

The present invention will be described specifically with reference to examples but is not limited to the examples. In the examples, "parts" and "%" denote "parts by weight" and "wt %" respectively. And, the viscosity indicates a value measured at 25° C.

Reference Example 1

Preparation of Emulsion Polymerized Silicone Emulsion A 250 parts of polyoxyethylene (2) lauryl ether sodium sulfate (27% aqueous solution) and 67.5 parts of lauryl sodium sulfate were homogeneously dissolved in 1695 parts of ion-exchanged water. To the homogeneous dissolved composition was added 2250 parts of $\alpha,\omega$-dihydroxydimethylsiloxane having a viscosity of 85 mPa·s, and they were stirred at 25° C. for one hour to conduct preliminary emulsification and treated by a pressure homogenizer (pressure of 550 kgf/cm2) three times to obtain an emulsion containing $\alpha,\omega$-dihydroxydimethylsiloxane.

The emulsion was cooled to15° C., 50.6 parts of a20% aqueous sulfuric acid solution was added to it, and polymerization reaction was conducted while stirring at 15° C. for nine hours. Then, 155 parts of a 10% aqueous sodium carbonate solution was added to adjust a pH value to 7 while stirring, and the polymerization reaction was stopped. An emulsion polymerized silicone emulsion A (E-8) containing high-molecular weight silicone was obtained. The obtained high-molecular weight silicone was measured for its viscosity to find 1,450,000 mPa·s at 25° C.

Reference Example 2

Preparation of Emulsion Polymerized Silicone Emulsion B

The emulsion polymerized emulsion B containing high-molecular weight silicone was obtained by the same procedure as that for the preparation of the silicone emulsion A except that the polymerization reaction was conducted at 15° C. for six hours. The obtained high-molecular weight silicone was measured for its viscosity to find 580,000 mPa·s at 25° C.

Reference Example 3

Preparation of Emulsion Polymerized Silicone Emulsion C

The emulsion polymerized emulsion C containing high-molecular weight silicone was obtained by the same procedure as that for the preparation of the silicone emulsion A except that the polymerization reaction was conducted at 15° C. for four hours. The obtained high-molecular weight silicone was measured for its viscosity to find 110,000 mPa·s at 25° C.

Example 1

62.2 parts of polyoxyethylene (2) lauryl ether sodium sulfate (27% aqueous solution) and 16.8 parts of lauryl sodium sulfate were homogeneously dissolved in 473 parts of ion-exchanged water. To the obtained solution were added 560 parts of decamethyl cyclopentasiloxane (D5) and 480 parts of the above-described emulsion polymerized silicone emulsion A, and they were stirred at 25° C. for one hour. Then, an emulsion (E-1) of high-molecular weight silicone containing D5 was obtained by treating by a pressure homogenizer (pressure of 550 kgf/cm$^2$) for three times.

The obtained emulsion was measured for its average particle diameter by a Coulter Counter N4 PLUS (particle diameter measuring equipment) to find 300 nm. Then, the obtained silicone emulsion (E-1) was used to prepare a shampoo composition having the components shown in Table 1.

Example 2

44.4 parts of polyoxyethylene (2) lauryl ether sodium sulfate (27% aqueous solution) and 12 parts of lauryl sodium sulfate were homogeneously dissolved in 338 parts of ion-exchanged water. To the obtained solution were added 400 parts of decamethyl cyclopenta siloxane (D5) and 800 parts of the emulsion polymerized silicone emulsion A, and they were stirred at 25° C. for one hour. Then, an emulsion (E-2) of high-molecular weight silicone containing D5 was obtained by treating by a pressure homogenizer (pressure of 550 kgf/cm$^2$) for three times.

The obtained emulsion was measured for its average particle diameter in the same manner as in Example 1 to find 240 nm. Then, the obtained silicone emulsion (E-2) was used to prepare a shampoo composition having the components shown in Table 1.

Example 3

17.9 parts of polyoxyethylene (2) lauryl ether sodium sulfate (27% aqueous solution) and 4.8 parts of lauryl sodium sulfate were homogeneously dissolved in 135 parts of ion-exchanged water. To the obtained solution were added 160 parts of decamethyl cyclopentasiloxane (D5) and 1280 parts of the emulsion polymerized silicone emulsion A, and they were stirred at 25° C. for one hour. Then, an emulsion (E-3) of high-molecular weight silicone containing D5 was obtained by treating by a pressure homogenizer (pressure of 550 kgf/cm$^2$) for three times.

The obtained emulsion was measured for its average particle diameter in the same manner as in Example 1 to find 220 nm. Then, the obtained silicone emulsion (E-3) was used to prepare a shampoo composition having the components shown in Table 1.

Example 4

Isoparaffinic hydrocarbon having a boiling point in a range of 201 to 265° C. was used instead of the decamethyl cyclopentasiloxane (D5) to obtain an emulsion (E-4) of high-molecular weight silicone containing the isoparaffinic hydrocarbon in the same manner as in Example 3.

The obtained emulsion was measured for its average particle diameter in the same manner as in Example 1 to find 220 nm. Then the obtained silicone emulsion (E-4) was used to prepare a shampoo composition having the components shown in Table 1.

Example 5

The emulsion polymerized silicone emulsion B was used instead of the emulsion polymerized silicone emulsion A to obtain an emulsion (E-5) of high-molecular weight silicone containing D5 in the same manner as in Example 3.

The obtained emulsion was measured for its average particle diameter in the same manner as in Example 1 to find 220 nm. Then, the obtained silicone emulsion (E-5) was used to prepare a shampoo composition having the components shown in Table 1.

Example 6

The emulsion polymerized silicone emulsion C was used instead of the emulsion polymerized silicone emulsion A to obtain an emulsion (E-6) of high-molecular weight silicone containing D5 in the same manner as in Example 3.

The obtained emulsion was measured for its average particle diameter in the same manner as in Example 1 to find 220 nm. Then, the obtained silicone emulsion (E-6) was used to prepare a shampoo composition having the components shown in Table 1.

Example 7

4.4 parts of polyoxyethylene (2) lauryl ether sodium sulfate (27% aqueous solution) and 1.2 parts of lauryl sodium sulfate were homogeneously dissolved in 34 parts of ion-exchanged water. To the obtained solution were added 40 parts of decamethyl cyclopentasiloxane (D5) and 1520 parts of the emulsion polymerized silicone emulsion A, and they were stirred at 25° C. for one hour. Then, an emulsion (E-7) of high-molecular weight silicone containing D5 was obtained by treating by a pressure homogenizer (pressure of 550 kgf/cm$^2$) for three times.

The obtained emulsion was measured for its average particle diameter in the same manner as in Example 1 to find 210 nm. Then, the obtained silicone emulsion (E-7) was used to prepare a shampoo composition having the components shown in Table 1.

Comparative Example 1

The above-described emulsion polymerized silicone emulsion A was used as it is as a silicone emulsion (E-8). The silicone emulsion (E-8) was measured for its average particle diameter in the same manner as in Example 1 to find 210 nm. And, the silicone emulsion (E-8) was used to prepare a shampoo composition having the components shown in Table 1.

Comparative Example 2

250 parts of polyoxyethylene (2) lauryl ether sodium sulfate (27% aqueous solution) and 67.5 parts of lauryl sodium sulfate were homogeneously dissolved in 1695 parts of ion-exchanged water. To the obtained solution were added 1800 parts of α, ω-dihydroxydimethylsiloxane having a viscosity of 85 mPa·s and 450 parts of the decamethyl cyclopentasiloxane (D5), and they were stirred at 25° C. for one hour to conduct preliminary emulsification and treated by a pressure homogenizer (pressure of 550 kgf/cm$^2$) three times to obtain an emulsion containing the α, ω-dihydroxydimethylsiloxane and the decamethyl cyclopentasiloxane (D5).

The emulsion was cooled to 15° C., 50.6 parts of a 20% aqueous sulfuric acid solution was added to it, and polymerization reaction was conducted while stirring at 15° C. for 18 hours. Then, 155 parts of a 10% aqueous sodium carbonate solution was added to adjust a pH value to 7 while stirring, and the polymerization reaction was stopped. Thus, an emulsion polymerized emulsion (E-9) containing high-molecular weight silicone was obtained.

The obtained high-molecular weight silicone was measured for its viscosity to find 1,140,000 mPa·s at 25° C. And, the obtained emulsion was measured for its average particle diameter in the same manner as in Example 1 to find 220 nm. Then, the obtained silicone emulsion (E-9) was used to prepare a shampoo composition having the components shown in Table 1.

Comparative Example 3

First, a D5 emulsion was prepared. Specifically, 89 parts of polyoxyethylene (2) lauryl ether sodium sulfate (27% aqueous solution) and 24 parts of lauryl sodium sulfate were homogeneously dissolved in 676 parts of ion-exchanged water. To the obtained solution was added 800 parts of decamethyl cyclopentasiloxane (D5), and they were stirred at 25° C. for one hour and treated by a pressure homogenizer (pressure of 550 kgf/cm$^2$) three times to obtain an emulsion (E-10) containing D5.

The obtained D5 emulsion (E-10) and the silicone emulsion (E-8) were mixed in the components shown in Table 1. The prepared emulsion was measured for its average particle diameter in the same manner as in Example 1 to find 210 nm. Then, the obtained emulsion was used to prepare a shampoo composition having the components shown in Table 1.

Comparative Example 4

To an emulsion machine having an anchor mixer and a disper mixer as one were charged 24 parts of polyoxyethylene (4) lauryl ether, 13 parts of polyoxyethylene (23) lauryl ether, 400 parts of polydimethylsiloxane having a viscosity of 500000 mPa·s and 100 parts of the decamethyl cyclopentasiloxane (D5), and they were stirred at 70° C. for one hour to homogeneously mix them. Then, 150 parts of ion-exchanged water was added, stirring was continued at 70° C. for one hour, and cooling was effected down to 25° C. while stirring. After stirring at 25° C. for two hours, 313 parts of ion-exchanged water was added to obtain an emulsion (E-11) containing high-molecular weight silicone.

The obtained emulsion was measured for its average particle diameter in the same manner as in Example 1 to find 300 nm. Then, the obtained silicone emulsion (E-11) was used to prepare a shampoo composition having the components shown in Table 1.

Next, the properties of the shampoo compositions prepared by the above-described examples 1-7 and comparative examples 1-4 were evaluated according to the following methods.

[Evaluation Method]

Ten panelists dipped 10 g of 25 cm long hair in water at 40° C., washed with 2 g of a shampoo composition for one minute, rinsed with water at 40° C. for 30 seconds and dried with a dryer to prepare hair samples. In the hair sample preparation stage, the individual panelists judged and evaluated "finger combing when washing hair", "finger combing when rinsing hair", "softness after drying" and "smoothness after drying".

The results are shown in Table 1. In individual columns of Table 1, (i), (ii), (v), (x) represent the following judged results.

[Finger Combing when Washing Hair]
(i): Eight or more panelists judged to be smooth and good finger combing without squeak.
(ii): Six to seven panelists judged to be smooth and good finger combing without squeak.
(v): Three to five panelists judged to be smooth and good finger combing without squeak.
(x): Two or less panelists judged to be smooth and good finger combing without squeak.

[Finger Combing when Rinsing]
(i): Eight or more panelists judged to be smooth and good finger combing without squeak.
(ii): Six to seven panelists judged to be smooth and good finger combing without squeak.
(v): Three to five panelists judged to be smooth and good finger combing without squeak.
(x): Two or less panelists judged to be smooth and good finger combing without squeak.

[Softness After Drying]
(i): Eight or more panelists judged to be soft and good touch.
(ii): Six to seven panelists judged to be soft and good touch.
(v): Three to five panelists judged to be soft and good touch.
(x): Two or less panelists judged to be soft and good touch.

[Smoothness After Drying]
(i): Eight or more panelists judged to be smooth and good finger combing.
(ii): Six to seven panelists judged to be smooth and good finger combing.
(v): Three to five panelists judged to be smooth and good finger combing.
(x): Two or less panelists judged to be smooth and good finger combing.

TABLE 1

| Components | Examples | | | | | | |
|---|---|---|---|---|---|---|---|
| (wt %) | 1 | 2 | 3 | 4 | 5 | 6 | 7 |
| E-1 | 4 | | | | | | |
| E-2 | | 4 | | | | | |
| E-3 | | | 4 | | | | |
| E-4 | | | | 4 | | | |
| E-5 | | | | | 4 | | |
| E-6 | | | | | | 4 | |
| E-7 | | | | | | | 4 |
| E-8 | | | | | | | |
| E-9 | | | | | | | |
| E-10 | | | | | | | |
| E-11 | | | | | | | |
| PLESS | 10 | 10 | 10 | 10 | 10 | 10 | 10 |
| LAAB | 3.5 | 3.5 | 3.5 | 3.5 | 3.5 | 3.5 | 3.5 |
| COFAMA | 2 | 2 | 2 | 2 | 2 | 2 | 2 |
| EGD | 2 | 2 | 2 | 2 | 2 | 2 | 2 |

TABLE 1-continued

| | | | | | | | |
|---|---|---|---|---|---|---|---|
| P-10 | 0.2 | 0.2 | 0.2 | 0.2 | 0.2 | 0.2 | 0.2 |
| SC | 2 | 2 | 2 | 2 | 2 | 2 | 2 |
| Paraben | 0.15 | 0.15 | 0.05 | 0.15 | 0.15 | 0.15 | 0.15 |
| Fragrance | 0.2 | 0.2 | 0.2 | 0.2 | 0.2 | 0.2 | 0.2 |
| PW | balance | balance | balance | balance | balance | balance | balance |
| TSVSC (%) | 2 | 2 | 2 | 2 | 2 | 2 | 2 |
| S/V S (wr) | 30/70 | 50/50 | 80/20 | 80/20 | 80/20 | 80/20 | 95/5 |
| SV (mPa·s) | 1450000 | 1450000 | 1450000 | 1450000 | 580000 | 110000 | 1450000 |
| EM | EP/ME | EP/ME | EP/ME | EP/ME | EP/ME | EP/ME | EP/ME |
| APDOE (nm) | 300 | 240 | 220 | 220 | 220 | 220 | 210 |
| ER (hw) | | | | | | | |
| FC/WH | (i) | (i) | (i) | (i) | (i) | (i) | (i) |
| FC/R | (i) | (i) | (i) | (i) | (i) | (i) | (i) |
| ER (ahd) | | | | | | | |
| Softness | (i) | (i) | (i) | (i) | (i) | (i) | (i) |
| Smoothness | (ii) | (ii) | (i) | (i) | (i) | (i) | (i) |

| Components | Comparative Examples | | | |
|---|---|---|---|---|
| (wt %) | 1 | 2 | 3 | 4 |
| E-1 | | | | |
| E-2 | | | | |
| E-3 | | | | |
| E-4 | | | | |
| E-5 | | | | |
| E-6 | | | | |
| E-7 | | | | |
| E-8 | 4 | | 3.2 | |
| E-9 | | 4 | | |
| E-10 | | | 0.8 | |
| E-11 | | | | 4 |
| PLESS | 10 | 10 | 10 | 10 |
| LAAB | 3.5 | 3.5 | 3.5 | 3.5 |
| COFAMA | 2 | 2 | 2 | 2 |
| EGD | 2 | 2 | 2 | 2 |
| P-10 | 0.2 | 0.2 | 0.2 | 0.2 |
| SC | 2 | 2 | 2 | 2 |
| Paraben | 0.15 | 0.15 | 0.15 | 0.15 |
| Fragrance | 0.2 | 0.2 | 0.2 | 0.2 |
| PW | balance | balance | balance | balance |
| TSVSC (%) | 2 | 2 | 2 | 2 |
| S/V S (wr) | 100/0 | 80/20 | 80/20 | 80/20 |
| SV (mPa·s) | 1450000 | 1140000 | 1450000 | 500000 |
| EM | EP | EP | EB | ME |
| APDOE (nm) | 210 | 220 | 210 | 300 |
| ER (hw) | | | | |
| FC/WH | (v) | (ii) | (v) | (x) |
| FC/R | (x) | (v) | (x) | (x) |
| ER (ahd) | | | | |
| Softness | (v) | (ii) | (v) | (v) |
| Smoothness | (ii) | (ii) | (ii) | (ii) |

PLESS = Polyoxyethylene (3) lauryl ether sodium sulfate
LAAB = Lauric acid amidopropyl betaine
COFAMA = Coconut oil fatty acid monoethanol amid
EGD = Ethylene glycol distearate
P-10 = Polyquaternium-10
SC = Sodium chloride
PW = Purified water
TSVSC = Total of silicone and volatile solvent contents
S/V S (wr) = Silicone/volatile solvent (weight ratio)
SV = Silicone viscosity
EM = Emulsification
APDOE = Average particle diameter of emulsion
ER (hw) = Evaluated results (hair washing)
FC/WH = Finger combing when washing hair
FC/R = Finger combing when rinsing
ER (ahd) = Evaluated results (after hair dried)
EP/ME = Emulsion polymerization/mechanical emulsion
EP = Emulsion polymerization
EB = Emulsion blending
ME = Mechanical emulsion

INDUSTRIAL APPLICABILITY

The hair cosmetic composition of the present invention can provide both wet hair and dry hair with outstanding smoothness and softness, and particularly provides outstanding finger combing at the time of rinsing the hair. Therefore, it is suitably used for shampoos, rinses, conditioners, treatments, hairstyling agents, hair mousses, hair creams, gels and the like.

What is claimed is:

1. A hair cosmetic composition, comprising:
    (A) a solvent-containing silicone emulsion which is prepared by emulsifying a mixture of an emulsion (a) and a volatile solvent (b), wherein the emulsion (a) contains a high-molecular-weight $\alpha, \omega$-dihydroxypolydimethylsiloxane, an anionic surfactant selected from the group consisting of polyoxyethylene (2) lauryl ether sulfate, polyoxyethylene (3) lauryl ether sulfate, and polyoxyethylene (4) lauryl ether sulfate, and/or lauryl sulfate, and water, wherein the high-molecular-weight $\alpha, \omega$-dihydroxypolydimethylsiloxane is obtained by emulsion polymerization of an $\alpha, \omega$-dihydroxydimethylsiloxane, the volatile solvent (b) is decamethyl cyclopentasiloxane or isoparaffinic hydrocarbon having a boiling point in a range of 201 to 265°;
    (B) one or more surfactants selected from an anionic surfactant, an amphoteric surfactant and a nonionic surfactant; and
    (C) water,
    wherein the solvent-containing silicone emulsion (A) is in the range of 0.1 to 10 wt % as a total amount of the high-molecular-weight $\alpha, \omega$-dihydroxypolydimethylsiloxane in the emulsion (a) and the volatile solvent (b), and the surfactant (B) is in the range of 0.05 to 40 wt %.

2. The hair cosmetic composition according to claim 1, wherein the solvent-containing silicone emulsion (A) has an average particle diameter of 150 to 350 nm.

* * * * *